US008614191B2

(12) United States Patent
Yang et al.

(10) Patent No.: US 8,614,191 B2
(45) Date of Patent: *Dec. 24, 2013

(54) USE OF ICAM-1 FOR PREVENTION OR TREATMENT OF NEUROLOGICAL DISEASES

(75) Inventors: Yoon-Sun Yang, Seoul (KR); Won Il Oh, Seoul (KR); Jong Wook Chang, Seoul (KR); Ji Hyun Kim, Seoul (KR)

(73) Assignee: Medipost Co., Ltd., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 13/365,022

(22) Filed: Feb. 2, 2012

(65) Prior Publication Data

US 2012/0196809 A1 Aug. 2, 2012

Related U.S. Application Data

(60) Provisional application No. 61/438,809, filed on Feb. 2, 2011, provisional application No. 61/541,487, filed on Sep. 30, 2011.

(51) Int. Cl.
*A61K 38/00* (2006.01)
(52) U.S. Cl.
USPC .................. 514/17.8; 514/17.7; 514/19.1
(58) Field of Classification Search
None
See application file for complete search history.

(56) References Cited

U.S. PATENT DOCUMENTS

| 5,733,542 | A | 3/1998 | Haynesworth et al. |
| 5,837,576 | A | 11/1998 | Chen et al. |
| 6,372,494 | B1 | 4/2002 | Naughton et al. |
| 6,900,299 | B1 | 5/2005 | Mohapatra et al. |
| 2004/0037775 | A1* | 2/2004 | Siahaan et al. .................. 424/9.1 |
| 2007/0037200 | A1 | 2/2007 | Ray et al. |
| 2007/0184038 | A1 | 8/2007 | Tennekoon et al. |
| 2008/0249157 | A1 | 10/2008 | Cossio Mora et al. |
| 2009/0035321 | A1* | 2/2009 | Springer et al. ........... 424/172.1 |
| 2009/0192105 | A1 | 7/2009 | McSwiggen et al. |

FOREIGN PATENT DOCUMENTS

| EP | 1 767 617 A1 | 3/2007 |
| KR | 10-2004-0016785 A | 2/2004 |
| KR | 10-2003-0069115 A | 7/2007 |
| WO | WO 00/53019 | 9/2000 |
| WO | WO-2007/084354 A2 | 7/2007 |
| WO | WO 2008072075 A2 * | 6/2008 |

OTHER PUBLICATIONS

Klementiev B et al. (2007) A neural cell adhesion molecule-derived peptide reduces neuropathological signs and cognitive impairment induced by Abeta25-35. Neuroscience, 145:209-224.*
Simmons D et al. (1988) ICAM, an adhesion ligand of LFA-1, is homologous to the neural cell adhesion molecule NCAM. Nature, 331:624-627.*
International Search Report mailed Sep. 20, 2012 in PCT International Application No. PCT/KR2012/000788, filed Feb. 1, 2012.
Kondziolka et al. "Transplantation of cultured human neuronal cells for patients with stroke," *Neurology* 55: 565-9 (2000).
International Written Opinion prepared by the Hungarian Intellectual Property Office mailed on Oct. 18, 2012 in related Singaporean Application No. 201103411-3.
Second Office Action issued by the State Intellectual Property Office of the People's Republic of China on Feb. 5, 2013 in related Chinese Application No. 200980154402.4.
Japanese Office Action dated Mar. 12, 2013 issued in related Japanese Application No. 2011-536252.
N. Liu et al., "Protective Effect of Activin A to the Injury of PC12 Cells Induced by Paraquat," *Chinese Journal of Clinical Neuroscience*, vol. 14, No. 1, 2006, pp. 25-32.
E. Sadot et al., "Short- and long-term mechanisms of tau regulation in PC12 cells," *Journal of Cell Science*, vol. 108, 1995, pp. 2857-2864.
J. Zhou, et al., "The co-culture system of MSCs and injured PC12 in vitro could inhibit the apoptosis of PC12," *Chin. J. Neurol*, Jul. 2006, vol. 39, No. 7, pp. 481-484.
L. Yi-zhao, et al., "Autologous bone mesenchymal stem cell transplatation for Alzheimer's disease in 4 cases," *Journal of Clinical Rehabilitative Tissue Engineering Research*, Oct. 21, 2008, vol. 12, No. 43, pp. 8431-8433.
Strelau et al., "Growth/Differentiation Factor-15/Macrophage Inhibitory Cytokine-1 is a Novel Trophic Factor for Midbriain Dopaminergic Neurons in Vivo," *J Neuroscience*, vol. 20, No. 23, Dec. 1, 2000, pp. 8597-8603.
Schindowski et al., "Regulation of GDF-15, a distant TGF-β superfamily member, in a mouse model of cerebral ischemia," *Cell Tissue Res*, 2011, vol. 343, pp. 399-409.
Ende et al., "Human Umbilical Cord Blood Cells Ameliorate Alzheimer's Disease in Transgenic Mice, A Brief Report," *Journal of Medicine*, vol. 32, Nos. 3 & 4, 2001, pp. 241-247.
Yang et al., "Mesenchymal stem/progenitor cells developed in cultures from UC blood," *Cytotherapy*, vol. 6, No. 5, 2004, pp. 476-486.
Minguell et al., "Biology and clinical utilization of mesenchymal progenitor cells", *Brazilian J of Med and Biol Research*, 2000, vol. 33, pp. 881-887.
Lijima-Ando, Kanae, et al., "Overexpression of Neprilysin Reduces Alzheimer Amyloid-β42 (Aβ42)-induced Neuron Loss and Intraneuronal Aβ42 Deposits but Causes a Reduction in cAMP-responsive Element-binding Protein-mediated Transcription, Age-dependent Axon Pathology, and Premature Death in *Drosophila*\*," *Journal of Biological Chemistry*, Jul. 4, 2008 vol. 283, No. 27, pp. 19066-19076.

(Continued)

*Primary Examiner* — Kimberly A Ballard
(74) *Attorney, Agent, or Firm* — Drinker Biddle & Reath LLP

(57) ABSTRACT

The present invention relates to a pharmaceutical composition for the prevention or treatment of neurological disorders, comprising an ICAM-1 (intercellular adhesion molecule-1) protein, or a fragment or a variant thereof as an active ingredient, which can increase the expression of neprilysin to remove amyloid-beta (Aβ), a cause of dementia, and is thus useful in preventing or treating a neurological disease including Alzheimer's disease.

4 Claims, 6 Drawing Sheets

(56) References Cited

OTHER PUBLICATIONS

Bae, Jae-Sung, et al., "Bone Marrow-Derived Mesenchymal Stem Cells Promote Neuronal Networks with Functional Synaptic Transmission After Transplantation into Mice with Neurodegeneration," Stem Cells, 2007, vol. 25, pp. 1307-1316.

S. Maudsley, et al., "Protein twists and turns in Alzheimer disease," Nature Medicine, Apr. 2006, vol. 12, No. 4, pp. 392-393.

M. Mattson, "Pathways towards and away from Alzheimer's disease," Nature, Aug. 5, 2004, vol. 430, pp. 631-639.

D. Kondziolka, M.D., et al., "Transplantation of cultured human neuronal cells for patients with stroke," Neurology, 2000, vol. 55, pp. 565-569.

M. Pittenger, et al., "Multilineage Potential of Adult Human Mesenchymal Stem Cells," Science, 1999, vol. 284, pp. 143-147.

L. Campos, et al., "Definition of Optimal Conditions for Collection and Cryopreservation of Umbilical Cord Hematopoietic Cells," Cryobiology, 1995, vol. 32, pp. 511-515.

K. Le Blanc, et al., "HLA expression and immunologic properties of differentiated and undifferentiated mesenchymal stem cells," Experimental Hematology, 2003, vol. 31, pp. 890-896.

HM Lazarus, et al., "Ex vivo expansion and subsequent infusion of human bone marrow-derived stromal progenitor cells (mesenchymal progenitor cells): implications for therapeutic use," Bone Marrow Transplantation, 1995, vol. 16, pp. 557-564.

C.J. Westermark, "What's hAPPening at synapses? The role of amyloid β-protein precursor and β-amyloid in neurological disorders," Molecular Psychiatry, 2013, vol. 18, pp. 425-434.

E. Blom et al., "Rapid Progression from Mild Cognitive Impairment to Alzheimer's Disease in Subjects with Elevated Levels of Tau in Cerebrospinal Fluid and the *APOE* ε64/ε4 Genotype," Dement Geriatr Cogn Discord, May 7, 2009, vol. 27, pp. 458-464.

G. Alves et al., "CSF amyloid-β and tau proteins, and cognitive performance, in early and untreated Parkinson's Disease: the Norwegian ParkWest study," J Neurol Neurosurg Psychiatry, 2010, vol. 81, pp. 1080-1086.

I. Mackenzie et al., "Senile plaques in temporal lobe epilepsy," Acta Neuropathol, 1994, vol. 87, pp. 504-510.

Bowman et al., (2008) "Alzheimer's disease and the blood-brain barrier: past, present and future," Aging Health, 4(1): 47-55.

Bantubungi et al., (2007) "Stem cell factor and mesenchymal and neural stem cell transplantation in a rat model of Huntington's Disease," Molecular and Cellular Neurosciences, 37(3): 454-470.

Cho Y H et al., (2006) "The behavioral effect of human mesenchymal stem cell transplantation in cold brain injured rats." Acta Neurochirurgica. Supplement, 99: 125-132.

Search Report dated Apr. 15, 2013 for European Patent Application No. 09 826 307.2.

U.S. Office Action dated Aug. 14, 2013, issued in U.S. Appl. No. 13/129,363.

Yu et al., "Induced expression of the new cytokine, activin A, in human monocytes: inhibition by glucocorticoids and retinoic acid," Immunology, 1996, vol. 88, pp. 368-374.

\* cited by examiner

SEQUENCE LISTING

```
<160> NUMBER OF SEQ ID NOS: 10

<210> SEQ ID NO 1
<211> LENGTH: 532
<212> TYPE: PRT
<213> ORGANISM: Homo sapiens
<220> FEATURE:
<221> NAME/KEY: misc_feature
<222> LOCATION: (241)..(241)
<223> OTHER INFORMATION: Xaa can be any naturally occurring amino acid
```

-continued

<400> SEQUENCE: 1

```
Met Ala Pro Ser Ser Pro Arg Pro Ala Leu Pro Ala Leu Leu Val Leu
1               5                   10                  15

Leu Gly Ala Leu Phe Pro Gly Pro Gly Asn Ala Gln Thr Ser Val Ser
            20                  25                  30

Pro Ser Lys Val Ile Leu Pro Arg Gly Gly Ser Val Leu Val Thr Cys
        35                  40                  45

Ser Thr Ser Cys Asp Gln Pro Lys Leu Leu Gly Ile Glu Thr Pro Leu
    50                  55                  60

Pro Lys Lys Glu Leu Leu Leu Pro Gly Asn Asn Arg Lys Val Tyr Glu
65                  70                  75                  80

Leu Ser Asn Val Gln Glu Asp Ser Gln Pro Met Cys Tyr Ser Asn Cys
                85                  90                  95

Pro Asp Gly Gln Ser Thr Ala Lys Thr Phe Leu Thr Val Tyr Trp Thr
            100                 105                 110

Pro Glu Arg Val Glu Leu Ala Pro Leu Pro Ser Trp Gln Pro Val Gly
        115                 120                 125

Lys Asn Leu Thr Leu Arg Cys Gln Val Glu Gly Gly Ala Pro Arg Ala
    130                 135                 140

Asn Leu Thr Val Val Leu Leu Arg Gly Glu Lys Glu Leu Lys Arg Glu
145                 150                 155                 160

Pro Ala Val Gly Glu Pro Ala Glu Val Thr Thr Thr Val Leu Val Arg
                165                 170                 175

Arg Asp His His Gly Ala Asn Phe Ser Cys Arg Thr Glu Leu Asp Leu
            180                 185                 190

Arg Pro Gln Gly Leu Glu Leu Phe Glu Asn Thr Ser Ala Pro Tyr Gln
        195                 200                 205

Leu Gln Thr Phe Val Leu Pro Ala Thr Pro Pro Gln Leu Val Ser Pro
    210                 215                 220

Arg Val Leu Glu Val Asp Thr Gln Gly Thr Val Val Cys Ser Leu Asp
225                 230                 235                 240

Xaa Leu Phe Pro Val Ser Glu Ala Gln Val His Leu Ala Leu Gly Asp
                245                 250                 255

Gln Arg Leu Asn Pro Thr Val Thr Tyr Gly Asn Asp Ser Phe Ser Ala
            260                 265                 270

Lys Ala Ser Val Ser Val Thr Ala Glu Asp Glu Gly Thr Gln Arg Leu
        275                 280                 285

Thr Cys Ala Val Ile Leu Gly Asn Gln Ser Gln Glu Thr Leu Gln Thr
    290                 295                 300

Val Thr Ile Tyr Ser Phe Pro Ala Pro Asn Val Ile Leu Thr Lys Pro
305                 310                 315                 320

Glu Val Ser Glu Gly Thr Glu Val Thr Val Lys Cys Glu Ala His Pro
                325                 330                 335

Arg Ala Lys Val Thr Leu Asn Gly Val Pro Ala Gln Pro Leu Gly Pro
            340                 345                 350

Arg Ala Gln Leu Leu Leu Lys Ala Thr Pro Glu Asp Asn Gly Arg Ser
        355                 360                 365

Phe Ser Cys Ser Ala Thr Leu Glu Val Ala Gly Gln Leu Ile His Lys
    370                 375                 380

Asn Gln Thr Arg Glu Leu Arg Val Leu Tyr Gly Pro Arg Leu Asp Glu
385                 390                 395                 400

Arg Asp Cys Pro Gly Asn Trp Thr Trp Pro Glu Asn Ser Gln Gln Thr
                405                 410                 415
```

```
Pro Met Cys Gln Ala Trp Gly Asn Pro Leu Pro Glu Leu Lys Cys Leu
            420                 425                 430

Lys Asp Gly Thr Phe Pro Leu Pro Ile Gly Glu Ser Val Thr Val Thr
        435                 440                 445

Arg Asp Leu Glu Gly Thr Tyr Leu Cys Arg Ala Arg Ser Thr Gln Gly
    450                 455                 460

Glu Val Thr Arg Glu Val Thr Val Asn Val Leu Ser Pro Arg Tyr Glu
465                 470                 475                 480

Ile Val Ile Ile Thr Val Val Ala Ala Val Ile Met Gly Thr Ala
                485                 490                 495

Gly Leu Ser Thr Tyr Leu Tyr Asn Arg Gln Arg Lys Ile Lys Lys Tyr
    500                 505                 510

Arg Leu Gln Gln Ala Gln Lys Gly Thr Pro Met Lys Pro Asn Thr Gln
    515                 520                 525

Ala Thr Pro Pro
    530

<210> SEQ ID NO 2
<211> LENGTH: 3249
<212> TYPE: DNA
<213> ORGANISM: Homo sapiens

<400> SEQUENCE: 2
caagcttagc ctggccggga acgggaggc gtggaggccg ggagcagccc ccggggtcat     60
cgccctgcca ccgccgcccg attgctttag cttggaaatt ccggagctga agcggccagc    120
gagggaggat gaccctctcg gcccgggcac cctgtcagtc cggaaataac tgcagcattt    180
gttccggagg ggaaggcgcg aggtttccgg gaaagcagca ccgcccttg gcccccaggt    240 ggctagcgct ataaaggatc acgcgcccca gtcgacgctg agctcctctg ctactcagag    300
ttgcaacctc agcctcgcta tggctcccag cagcccccgg cccgcgctgc ccgcactcct    360
ggtcctgctc ggggctctgt tcccaggacc tggcaatgcc cagacatctg tgtccccctc    420
aaaagtcatc ctgccccggg gagctccgt gctggtgaca tgcagcacct cctgtgacca    480
gcccaagttg ttgggcatag agccccgtt gcctaaaaag gagttgctcc tgcctgggaa    540
caaccggaag gtgtatgaac tgagcaatgt gcaagaagat agccaaccaa tgtgctattc    600
aaactgccct gatgggcagt caacagctaa accttcctc accgtgtact ggactccaga    660
acgggtggaa ctggcacccc tcccctcttg gcagccagtg ggcaagaacc ttaccctacg    720
ctgccaggtg gagggtgggg cacccgggc aacctcacc gtggtgctgc tccgtgggga    780
gaaggagctg aaacgggagc agctgtgggg ggagcccgct gaggtcacga ccacggtgct    840
ggtgaggaga gatcaccatg gagccaattt ctcgtgccgc actgaactgg acctgcggcc    900
ccaagggctg gagctgtttg agaacaccct ggccccctac cagctccaga cctttgtcct    960
gccagcgact ccccacaac ttgtcagccc ccgggtccta gaggtggaca cgcaggggac   1020
cgtggtctgt tccctggacg ggctgttccc agtctcggag gcccaggtcc acctggcact   1080
gggggaccag aggttgaacc ccacagtcac ctatggcaac gactccttct cggccaaggc   1140
ctcagtcagt gtgaccgcag aggacgaggg cacccagcgg ctgacgtgtg cagtaatact   1200
ggggaaccag agccaggaga cactgcagac agtgaccatc tacagctttc ggcgcccaa    1260 cgtgattctg acgaagccag aggtctcaga agggaccgag gtgacagtga agtgtgaggc   1320 ccacccctaga gccaaggtga cgctgaatgg ggttccagcc cagccactgg ccccgagggc   1380
ccagctcctg ctgaaggcca ccccagagga caacgggcgc agcttctcct gctctgcaac   1440
```

-continued

```
cctggaggtg gccggccagc ttatacacaa gaaccagacc cgggagcttc gtgtcctgta    1500
tggcccccga ctggacgaga gggattgtcc gggaaactgg acgtggccag aaaattccca    1560
gcagactcca atgtgccagg cttggggaa cccattgccc gagctcaagt gtctaaagga    1620
tggcactttc ccactgccca tcggggaatc agtgactgtc actcgagatc ttgagggcac    1680
ctacctctgt cgggccagga gcactcaagg ggaggtcacc cgcaaggtga ccgtgaatgt    1740
gctctccccc cggtatgaga ttgtcatcat cactgtggta gcagccgcag tcataatggg    1800
cactgcaggc ctcagcacgt acctctataa ccgccagcgg aagatcaaga aatacagact    1860
acaacaggcc caaaaaggga cccccatgaa accgaacaca caagccacgc ctccctgaac    1920
ctatcccggg acagggcctc ttcctcggcc ttcccatatt ggtggcagtg gtgccacact    1980
gaacagagtg gaagacatat gccatgcagc tacacctacc ggccctggga cgccggagga    2040
cagggcattg tcctcagtca gatacaacag catttggggc catggtacct gcacacctaa    2100
aacactaggc cacgcatctg atctgtagtc acatgactaa gccaagagga aggagcaaga    2160
ctcaagacat gattgatgga tgttaaagtc tagcctgatg agaggggaag tggtggggga    2220
gacatagccc caccatgagg acatacaact gggaaatact gaaacttgct gcctattggg    2280
tatgctgagg ccccacagac ttacagaaga agtggccctc cataggacatg tgtagcatca    2340 aaacacaaag gcccacactt cctgacggat gccagcttgg gcactgctgt ctactgaccc    2400
caacccttga tgatatgtat ttattcattt gttattttac cagctattta ttgagtgtct    2460
tttatgtagg ctaaatgaac ataggtctct ggcctcacgg agctcccagt cctaatcaca    2520
ttcaaggtca ccaggtacag ttgtacaggt tgtacactgc aggagagtgc ctggcaaaaa    2580
gatcaaatgg ggctgggact tctcattggc caacctgcct ttccccagaa ggagtgattt    2640
ttctatcggc acaaaagcac tatatggact ggtaatggtt acaggttcag agattaccca    2700
gtgaggcctt attcctccct tccccccaaa actgacacct tgttagcca cctccccacc    2760 cacatacatt tctgccagtg ttcacaatga cactcagcgg tcatgtctgg acatgagtgc    2820
ccagggaata tgcccaagct atgccttgtc ctcttgtcct gtttgcattt cactgggagc    2880
ttgcactatg cagctccagt ttcctgcagt gatcagggtc ctgcaagcag tggggaaggg    2940
ggccaaggta ttggaggact ccctcccagc tttggaagcc tcatccgcgt gtgtgtgtgt    3000
gtgtatgtgt agacaagctc tcgctctgtc acccaggctg gagtgcagtg gtgcaatcat    3060
ggttcactgc agtcttgacc ttttgggctc aagtgatcct cccacctcag cctcctgagt    3120
agctgggacc ataggctcac aacaccacac ctggcaaatt tgattttttt ttttttcca    3180 gagacggggt ctcgcaacat tgcccagact tcctttgtgt tagttaataa agctttctca    3240
actgccaaa                                                            3249
```

<210> SEQ ID NO 3
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 3
cccccaggtg gctagcgcta                                                20

<210> SEQ ID NO 4
<211> LENGTH: 20
<212> TYPE: DNA
<213> ORGANISM: Artificial Sequence

```
<220> FEATURE:
<223> OTHER INFORMATION: Synthetic oligonucleotide primer

<400> SEQUENCE: 4
gtgcccaagc tggcatccgt                                              20

<210> SEQ ID NO 5
<211> LENGTH: 30
<212> TYPE: DNA
<213> ORGANISM: Artificial Sequence
<220> FEATURE:
<223> OTHER INFORMATION: Synthetic oligonucleotide primer

<400> SEQUENCE: 5
ccgccgcata tgcagacatc tgtgtccccc                                   30

<210> SEQ ID NO 6
<211> LENGTH: 36
<212> TYPE: DNA
<213> ORGANISM: Artificial Sequence
<220> FEATURE:
<223> OTHER INFORMATION: Synthetic oligonucleotide primer

<400> SEQUENCE: 6
cccccccccc ggggatcctc atcagatgac aatctc                            36

<210> SEQ ID NO 7
<211> LENGTH: 33
<212> TYPE: DNA
<213> ORGANISM: Artificial Sequence
<220> FEATURE:
<223> OTHER INFORMATION: Synthetic oligonucleotide primer

<400> SEQUENCE: 7
cattcgggat cctcatcact ggccggccac ctc                               33

<210> SEQ ID NO 8
<211> LENGTH: 33
<212> TYPE: DNA
<213> ORGANISM: Artificial Sequence
<220> FEATURE:
<223> OTHER INFORMATION: Synthetic oligonucleotide primer

<400> SEQUENCE: 8
cggggatcct catcactcct ggctctggtt ccc                               33

<210> SEQ ID NO 9
<211> LENGTH: 33
<212> TYPE: DNA
<213> ORGANISM: Artificial Sequence
<220> FEATURE:
<223> OTHER INFORMATION: Synthetic oligonucleotide primer

<400> SEQUENCE: 9
cggcggggat cctcatcaaa acagctccag ccc                               33

<210> SEQ ID NO 10
<211> LENGTH: 532
<212> TYPE: PRT
<213> ORGANISM: Pan troglodytes

<400> SEQUENCE: 10

Met Ala Pro Ser Ser Pro Arg Pro Ala Leu Pro Ala Leu Leu Val Leu
1               5                   10                  15

Leu Gly Ala Leu Phe Pro Gly Pro Gly Asn Ala Gln Thr Ser Val Ser
            20                  25                  30
```

-continued

```
Pro Pro Lys Val Ile Leu Pro Arg Gly Gly Ser Val Gln Val Thr Cys
        35                  40                  45

Ser Thr Ser Cys Asp Gln Pro Asp Leu Leu Gly Ile Glu Thr Pro Leu
 50                  55                  60

Pro Lys Lys Glu Leu Leu Leu Gly Gly Asn Asn Trp Lys Val Tyr Glu
 65                  70                  75                  80

Leu Ser Asn Val Gln Glu Asp Ser Gln Pro Met Cys Tyr Ser Asn Cys
                 85                  90                  95

Pro Asp Gly Gln Ser Thr Ala Lys Thr Phe Leu Thr Val Tyr Trp Thr
                100                 105                 110

Pro Glu Arg Val Glu Leu Ala Pro Leu Pro Ser Trp Gln Pro Val Gly
            115                 120                 125

Lys Asp Leu Thr Leu Arg Cys Gln Val Glu Gly Gly Ala Pro Arg Ala
        130                 135                 140

Asn Leu Thr Val Val Leu Leu Arg Gly Glu Lys Glu Leu Lys Arg Glu
145                 150                 155                 160

Pro Ala Val Gly Glu Pro Ala Glu Val Thr Thr Thr Val Leu Val Glu
                165                 170                 175

Arg Asp His His Gly Ala Asn Phe Ser Cys Arg Thr Glu Leu Asp Leu
            180                 185                 190

Arg Pro Gln Gly Leu Gln Leu Phe Glu Asn Thr Ser Ala Pro His Gln
        195                 200                 205

Leu Gln Thr Phe Val Leu Pro Ala Thr Pro Gln Leu Val Ser Pro
    210                 215                 220

Arg Val Leu Glu Val Asp Thr Gln Gly Thr Val Val Cys Ser Leu Asp
225                 230                 235                 240

Gly Leu Phe Pro Val Leu Glu Ala Gln Val His Leu Ala Leu Gly Asp
                245                 250                 255

Gln Arg Leu Asn Pro Thr Val Thr Tyr Gly Asn Asp Ser Phe Ser Ala
            260                 265                 270

Lys Ala Ser Val Ser Val Thr Ala Glu Asp Glu Gly Thr Gln Arg Leu
        275                 280                 285

Thr Cys Ala Val Ile Leu Gly Asn Gln Ser Arg Glu Thr Leu Gln Thr
290                 295                 300

Val Thr Ile Tyr Ser Phe Pro Ala Pro Asn Val Ile Leu Thr Lys Pro
305                 310                 315                 320

Glu Val Ser Glu Gly Thr Glu Val Thr Val Lys Cys Glu Ala His Pro
                325                 330                 335

Arg Ala Lys Val Thr Leu Asn Gly Val Pro Ala Gln Pro Val Gly Pro
            340                 345                 350

Arg Val Gln Leu Leu Leu Lys Ala Thr Pro Glu Asp Asn Gly Arg Ser
        355                 360                 365

Phe Ser Cys Ser Ala Thr Leu Glu Val Ala Gly Gln Leu Ile His Lys
370                 375                 380

Asn Gln Thr Arg Glu Leu Arg Val Leu Tyr Gly Pro Arg Leu Asp Glu
385                 390                 395                 400

Arg Asp Cys Pro Gly Asn Trp Thr Trp Pro Glu Asn Ser Gln Gln Thr
                405                 410                 415

Pro Met Cys Gln Ala Ser Gly Asn Pro Leu Pro Glu Leu Lys Cys Leu
            420                 425                 430

Lys Asp Gly Thr Phe Pro Leu Pro Val Gly Glu Ser Val Thr Val Thr
        435                 440                 445

Arg Asp Leu Glu Gly Thr Tyr Leu Cys Arg Ala Arg Ser Thr Gln Gly
450                 455                 460
```

-continued

```
Glu Val Thr Arg Lys Val Thr Val Asn Val Leu Ser Pro Arg Tyr Glu
465                 470                 475                 480

Ile Val Ile Ile Thr Val Val Ala Ala Ala Val Ile Met Gly Thr Ala
                485                 490                 495

Gly Leu Ser Thr Tyr Leu Tyr Asn Arg Gln Arg Lys Ile Arg Lys Tyr
                500                 505                 510

Arg Leu Gln Gln Ala Gln Lys Gly Thr Pro Met Lys Pro Asn Thr Gln
        515                 520                 525

Ala Thr Pro Pro
        530
```

USE OF ICAM-1 FOR PREVENTION OR TREATMENT OF NEUROLOGICAL DISEASES

CROSS-REFERENCE

This application claims the benefits of U.S. Provisional Application No. 61/438,809 filed on Feb. 2, 2011 and U.S. Provisional Application No. 61/541,487 filed on Sep. 30, 2011, all of which are incorporated herein by reference.

REFERENCE TO A SEQUENCE LISTING

A sequence listing having SEQ ID NOS: 1-10 is incorporated by reference hereto.

BACKGROUND OF THE INVENTION

Alzheimer's disease is manifested by the destruction of brain cells, partlydue to accumulation of amyloid-beta (Aβ) protein in the brain. Alzheimer's disease progresses in stages and gradually deteriorates the faculties of memory, reasoning, judgment and speech, as well as an ability to carry out simple tasks.

Parkinson's disease is manifested by the destruction of a specialized brain cells, known as the dopaminergic neurons. Loss of dopaminergic neurons lead to clinical symptoms including, but not limited to, the loss of motor control. The cause of onset of Parkinson's disease is not known.

Depression or major depressive disorder is also a disease of brain. The diagnosis is based on the patient's self-reporting experiences including low mood, low self-esteem, and loss of interest or pleasure in various activities.

Epilepsy is a neurological disorder of the brain. Patients with epilepsy suffer from frequent, unpredictable seizures. An epileptic episode is marked by an abnormally increased neuronal activity in the brain.

Multiple sclerosis is manifested by the inflammation of the myelin sheaths around the axons of the brain and the spinal cord. Demyelination leads to, over time, the loss of various physical and cognitive functions.

Mania is a state of abnormally elevated or irritable mood, often lasting for a week or more. Patients suffering from manic episode have been treated with drugs targeting on neurotransmission.

Lou Gehrig's disease, also known as amyotrophic lateral sclerosis is a form of motor neuron disease manifested by the degeneration of neurons in the spinal cord. Patients suffering from the disease experience muscle atrophy, weakness, and breathing difficulties.

Mild cognitive impairment (MCI, also known as incipient dementia, or isolated memory impairment) is a brain-function syndrome involving the onset and evolution of cognitive impairments beyond those expected based on the age and education of the individual, but which are not significant enough to interfere with their daily activities. It is often found to be a transitional stage between normal aging and dementia. Although MCI can present with a variety of symptoms, when memory loss is the predominant symptom it is termed "amnestic MCI" and is frequently seen as a prodromal stage of Alzheimer's disease. Studies suggest that these individuals tend to progress to probable Alzheimer's disease at a rate of approximately 10% to 15% per year.

Multi-infarct dementia is one type of vascular dementia. Vascular dementia is the second most common form of dementia after Alzheimer's disease (AD) in older adults. Multi-infarct dementia (MID) is thought to be an irreversible form of dementia, and its onset is caused by a number of small strokes or sometimes, one large stroke preceded or followed by other smaller strokes. The term refers to a group of syndromes caused by different mechanisms all resulting in vascular lesions in the brain. Early detection and accurate diagnosis are important, as vascular dementia is at least partially preventable.

Dementia with Lewy bodies (DLB), also known under a variety of other names including Lewy body dementia, diffuse Lewy body disease, cortical Lewy body disease, and senile dementia of Lewy type, is a type of dementia closely allied to both Alzheimer's and Parkinson's Diseases. It is characterized anatomically by the presence of Lewy bodies, clumps of alpha-synuclein and ubiquitin protein in neurons, detectable in post-mortem brain biopsies. Lewy Body dementia affects 1.3 million individuals in the United States alone.

Neprilysin is an enzyme that degrades amyloid beta peptide. Deficiency of neprilysin accelerates the extracellular accumulation of amyloid. An increase in neprilysin expression reduces Aβ peptides.

Intracellular Adhesion Molecule-1 (ICAM-1) is a membrane glycoprotein encoded by the ICAM1 gene. Mice deficient of ICAM1 gene developed normally, were fertile, and had a moderate granulocytosis, but exhibited impaired neutrophil emigration to chemical stimulus and abnormalities in inflammatory responses.

SUMMARY OF THE INVENTION

Described herein is a pharmaceutical composition for the prevention or treatment of a neurological disease, comprising an ICAM-1 (intercellular adhesion molecule-1) protein, or a fragment or a variant thereof as an active ingredient. In one embodiment, the ICAM-1 protein of said composition has the amino acid sequence of SEQ. ID. NO.: 1 or the amino acid sequence from which a signal peptide corresponding to the 1st to 27th amino acid residues is removed. In another embodiment, the fragment of the ICAM-1 protein has a biological activity equivalent to that of the ICAM-1 protein. In another embodiment, the variant of the ICAM-1 protein has the amino acid sequence of SEQ. ID. NO.: 1 in which one or more amino acids are substituted, deleted, inserted and/or added, and has a biological activity equivalent to that of the ICAM-1 protein. In another embodiment, the variant of the ICAM-1 protein has an amino acid sequence identical to at least about 90%, 93%, 95%, 96%, 97%, 98% or 99% of the ICAM-1 protein having the amino acid sequence of SEQ. ID. NO.: 1, and has a biological activity equivalent to that of the ICAM-1 protein. In another embodiment, the ICAM-1 protein, or the fragment or the variant thereof induces the expression of neprilysin (NEP) to promote degradation of amyloid-beta (Aβ). In another embodiment, the neurological disease is a disease caused by at least one selected from the group consisting of formation of amyloid-beta plaque in neurons, hyperphosphorylation of tau protein in neurons, damage to neurites, reduction in expression of neprilysin in neurons, and a combination thereof. In another embodiment, the neurological disease is selected from the group consisting of Alzheimer's disease, Parkinson's disease, depression, epilepsy, multiple sclerosis, mania, Lou Gehrig's disease, mild cognitive impairment, multi-infarct dementia, and dementia with Lewy bodies.

Described herein is a method of preventing or treating a neurological disease in a subject, comprising administering to the subject in need thereof an ICAM-1 protein, or a fragment or a variant thereof.

Described herein is a method of increasing the expression of neprilysin in neurons, comprising co-culturing with neurons an ICAM-1 protein, or a fragment or a variant thereof.

Described herein is a method of increasing the expression of neprilysin in a subject, comprising administering to the subject an ICAM-1 (intercellular adhesion molecule-1) protein, or a fragment or a variant thereof.

Described herein is a composition comprising an ICAM-1 protein, or a fragment or a variant thereof, wherein said protein, fragment, or a variant thereof can increase the expression of neprilysin in neurons to remove amyloid-beta peptides, a cause of dementia, and is thus useful in preventing or treating a neurological disease including Alzheimer's disease.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
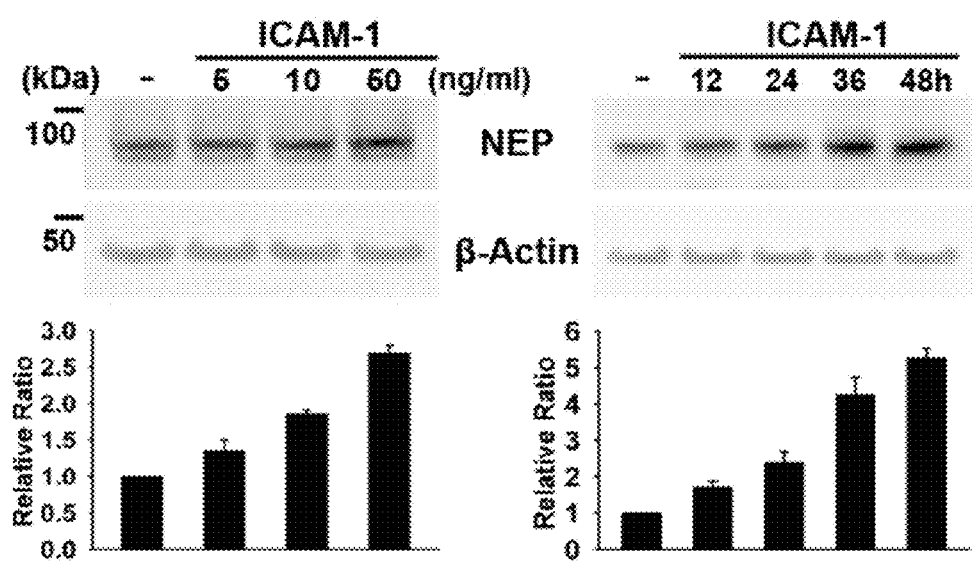
FIG. 1 illustrates the effect of ICAM-1 on the expression of neprilysin in microglial cells.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Unless characterized differently, technical and scientific terms used herein have the same meaning as commonly understood by one of ordinary skill in the art to which this invention belongs.

The term "about" in relation to a reference numerical value includes a range of values plus or minus 15% from that value. For example the amount "about 10" includes amounts from 8.5 to 11.5.

The term "amyloid-beta (Aβ)" refers to a major element of amyloid plaque found in the brain of a patient having Alzheimer's disease. An Aβ can be a peptide including an amino acid derived from the C-terminal of amyloid precursor protein (APP) that is a transmembrane glycoprotein. An Aβ can be produced from APP by a continuous operation of β-secretase and γ-secretase. An Aβ can be 39 to 43 amino acids, or 40 to 42 amino acids. An Aβ can comprise 672-713 residues (Aβ42) or 672-711 residues (Aβ40) of the amino acid sequence of NCBI Accession No.: NP_000475. An Aβ can be a human amyloid-beta A4 protein isoform precursor. An Aβ can be derived from a mammal. An Aβ can be derived from a human or a mouse. An Aβ can be recombinantly produced.

The term "tau protein" refers to a microtubule-associated protein found in neurons of the central nervous system. A tau protein interacts with tubulin to stabilize microtubule and promotes tubulin assembly of the microtubule. A cerebral tissue can include six different tau isoforms. Hyperphosphorylation of a tau protein is related to the development of Alzheimer's disease. A tau protein can be highly soluble. In humans, a tau protein can be found in neurons rather than non-neuron cells. A protein can be involved in the stabilization of axonal microtubule. A tau protein can be microtubule-associated protein tau isoform 2 having the amino acid sequence of NCBI Accession No: NP_005901. A tau protein can be derived from a mammal. A tau protein can be derived from a human or a mouse. A tau protein can be recombinantly produced.

The term "neprilysin" refers to a zinc-dependent metalloprotease enzyme decomposing a large number of small, secreted peptides. Neprilysin can decompose amyloid-beta that causes Alzheimer's disease if amyloid-beta is abnormally folded and aggregated in neural tissues. A neprilysin can be a peptide having the amino acid sequence of NCBI Accession No: NP_000893. Neprilysin can be derived from a mammal. Neprilysin can be derived from a human or a mouse. Neprilysin can be recombinantly produced.

ICAM-1

Described herein is a pharmaceutical composition comprising an ICAM-1 (intercellular adhesion molecule-1) protein, or a fragment or a variant thereof, as an active ingredient.

In one aspect, an ICAM-1 useful for compositions and methods described herein includes a naturally occurring ICAM-1. In one embodiment, a naturally occurring ICAM-1 includes, but is not limited to, an ICAM-1 having a wild-type amino acid sequence of an ICAM-1 normally associated with an animal. In another embodiment, a naturally occurring ICAM-1 includes, but is not limited to, a naturally occurring variant of an ICAM-1. In one embodiment, a naturally occurring variant is an allelic variant. In another embodiment, a naturally occurring variant is a polymorphic variant. In another aspect, an ICAM-1 useful for compositions and methods described herein includes a mutant of an ICAM-1. In one embodiment, a mutant can be an ICAM-1 having a mutation found in nature. In another embodiment, a mutation can be a mutation artificially introduced to an ICAM-1. In one embodiment, a mutation can be a mutation introduced to the nucleic acid sequence of an ICAM-1, either with or without having an effect of replacing, deleting, or inserting one or more amino acid to a nucleic sequence encoding ICAM-1.

In one aspect, an ICAM-1 useful for compositions and methods described herein includes polypeptide sequences encoding an ICAM-1 of an animal. An animal encoding an ICAM-1 can include, but is not limited to, *Homo sapiens, Mus musculus, Rattus norvegicus, Bos taurus, Pan troglodytes, Canis lupus familiaris, Sus scrofa, Oryctolagus*

*cuniculus, Macaca mulatta, Nomascus leucogenys, Cricetulus griseus, Gorilla gorilla, Pongo abelii, Callithrix jacchus,* and *Ailuropoda melanoleuca*. A variety of ICAM-1 peptide sequences discovered in these animals are available in public databases including National Center for Biotechnology Information (NCBI). In one embodiment, an ICAM-1 useful for compositions and methods described herein is an animal ICAM-1 with a sequence corresponding to a GenBank Accession Number. A GenBank Accession Number of an ICAM-1 useful for compositions and methods described herein includes, but is not limited to, P13597.1, Q00238.1, CAA41977.1, AAB19978.1, P05362.2, NP_037099.1, NP_000192.2, NP_776773.1, NP_001009946.1, P33729.2, Q5NKV4.1, Q28806.2, Q95132.1, NP_001040600.1, DAA28002.1, Q5NKV9.1, Q5NKV6.1, AAA92551.1, NP_034623.1, NP_998981.1, AAA37875.1, AAF80287.1, NP_001003291.1, AAD13617.1, NP_001009731.1, ACJ49146.1, AAB51145.1, BAD04920.1, 1IAM_A, 1MQ8_C, 1MQ8_A, 3TCX_b, 3TCX_a, 3TCX_Z, 3TCX_Y, 3TCX_X, 3TCX_W, 3TCX_V, 3TCX_U, 3TCX_T, 3TCX_S, 3TCX_R, 3TCX_Q, 3TCX_P, 3TCX_O, 3TCX_N, 3TCX_M, 3TCX_L, 3TCX_K, 3TCX_J, 3TCX_I, 3TCX_H, 3TCX_G, 3TCX_F, 3TCX_E, 3TCX_D, 3TCX_C, 3TCX_B, 3TCX_A, 2OZ4_H, 2OZ4_L, 2OZ4_A, 1P53_A, 1P53_B, 1MQ8_D, 1MQ8_B, 1IC1_B, 1IC1_A, CAA30051.1, 1D3E_I, 1D3E_4, 1D3E_3, 1D3E_2, 1D3E_1, 1D3L_A, NP_037021.1, 1DG1_4, 1DG1_3, 1DG1_2, 1DG1_1, 1DG1_R, NP_034624.1, NP_001032869.2, NP_001186763.1, NP_542413.1, NP_001069.1, P90489.1, NP_579840.1, 3EO9_H, 3EO9_L, 3EOB_J, 3EB_B, 3EOB_A, 3EOB_I, 3EOB_H, 3EOB_L, 3EOA_J, 3EOA_B, 3EOA_A, 3EOA_I, 3EOA_H, 3EOA_L, BAA00759.1, CAA36507.1, NP_999056.1, NP_036843.1, AAA84866.1, 3HI6_Y, 3HI6_X, 3HI6_L, 3HI6_H, 3HI6_B, 3HI6_A, 3HI5_L, 3HI5_H, AAA37876.1, 1MJN_A, AAA35415.1, 1MQA_A, 1MQ9_A, NP_001139280.1, NP_000623.2, NP_000425.1, EAW72950.1, EAW72949.1, NP_938033.1, NP_005408.1, NP_002219.1, P29533.1, P19320.1, Q9UMF0.3, P13598.2, NP_035823.3, NP_937882.1, NP_003871.1, NP_001107852.1, NP_002200.2, NP_001093259.1, NP_001093258.1, NP_001093257.1, NP_000864.2, NP_001093256.1, NP_038900.1, NP_058577.1, NP_001126200.1, NP_001095120.1, NP_001094628.1, NP_001094501.1, NP_776909.1, NP_612405.2, EHH50108.1, EHH14990.1, NP_001075621.1, EHB02165.1, XP_003479223.1, XP_003409421.1, AEH17929.1, NP_001003298.1, ADS87907.1, ADS87821.1, ADS11235.1, XP_002928199.1, XP_001135527.2, XP_003260168.1, XP_003260167.1, XP_003260166.1, AED70916.1, 1YO4_A, 1Z7Z_I, 1VCA_B, 1VCA_A, BAE25364.1, BAE37132.1, BAJ20764.1, AAA61269.1, AAA52709.1, AAA42332.1, AAA40545.1, AAA51917.1, XP_002801716.1, XP_001107860.1, XP_001107924.1, DAA31477.1, DAA31439.1, XP_002751186.1, XP_002751185.1, XP_002751184.1, AAO52742.1, AAG30280.1, AAC97931.1, AAH89812.1, AAH81837.1, EFB17343.1, AAH11159.2, AAH29823.1, AAA61270.1, AAY99622.1, AAI51460.1, AAM96190.1, AAH85003.1, AAH68490.2, AAH17276.3, AAA16921.1, 1D3I_I, ACP59454.1, CAJ18580.1, ACE87430.1, ACE86744.1, CAH92063.1, ABS85192.1, BAF84421.1, BAD96986.1, EDL82023.1, EDL78334.1, EDL12389.1, EDL12388.1, CAA34621.1, CAA45254.1, CAA47989.1, AAX04663.1, AAQ80666.1, AAE84809.1, AAE84808.1, BAB19782.1, BAB19650.1, 226347, CAA37218.1, CAA33630.1, Q28260.1, NP_776975.1, NP_000946.2, P29534.1, AAB46863.1, NP_997404.1, NP_997403.1, NP_065393.1, NP_722550.1, NP_008939.1, NP_999564.1, EAW94220.1, EAW94219.1, EAW94218.1, EAW94217.1, EAW94216.1, NP_035012.2, NP_001171744.1, NP_059430.2, NP_001020083.1, NP_000566.3, NP_001703.2, NP_006524.1, NP_004753.1, P15941.3, P20701.3, Q86YJ5.2, P09450.1, NP_065109.1, NP_032223.2, NP_004045.1, Q82122.4, NP_001192273.1, NP_001171745.1, NP_001171742.1, NP_001535.1, XP_542074.2, NP_003250.3, NP_004193.1, NP_001025459.1, NP_001003301.1, NP_999011.1, NP_071614.1, NP_003114.1, NP_001164621.1, NP_001117196.1, NP_001117195.1, NP_001091731.1, NP_031645.2, NP_001007726.1, NP_999187.1, NP_620234.1, NP_032442.1, EHH59189.1, EHH29618.1, NP_001075902.1, NP_001034221.1, NP_446310.1, Q28730.1, NP_071772.1, NP_001009166.1, NP_001189482.1, Q60625.1, NP_076381.1, XP_003514828.1, XP_003512840.1, EHB03341.1, XP_003123268.1, XP_003123292.3, NP_001727.1, NP_032345.2, NP_004219.3, NP_059431.1, P10922.4, AEN34099.1, AEN34098.1, EGW02598.1, ADT46952.1, ADS73661.1, ADS58865.1, ADS30919.1, NP_001165550.1, ADT46951.1, ADS58866.1, ADS11236.1, AAC50959.1, NP_987103.1, AEL21381.1, AEH21939.1, AEH17956.1, AEH17955.1, AEH17954.1, AEH17953.1, AEH17952.1, AEH17951.1, AEH17950.1, AEH17949.1, AEH17948.1, AEH17947.1, AEH17946.1, AEH17945.1, AEH17944.1, AEH17943.1, AEH17942.1, AEH17941.1, AEH17940.1, AEH17939.1, AEH17938.1, AEH17937.1, AEH17936.1, AEH17935.1, AEH17934.1, AEH17933.1, AEH17932.1, AEH17931.1, AEH17930.1, AEF79448.1, AEF79447.1, AEF79446.1, AEF79445.1, AEF79444.1, AEF79443.1, AEF75643.1, XP_002921422.1, XP_003262690.1, XP_003262689.1, XP_003262688.1, XP_001922015.3, XP_002661307.2, XP_694556.3, 1RMF_L, 1Z7Z_5, 1Z7Z_4, 1Z7Z_3, 1Z7Z_2, 1Z7Z_1, 1RMF_H, 3BN3_B, 2P28_B, 2P28_A, 2P26_A, 1ZXQ_A, 1UOT_P, 1VSC_B, 1VSC_A, BAE31310.1, BAE31287.1, BAE31286.1, BAE30990.1, BAE40221.1, BAE29272.1, BAE29266.1, BAE29079.1, BAE29059.1, BAE42944.1, BAE30219.1, BAE22394.1, BAE42504.1, BAE42493.1, BAC26834.1, BAJ20559.1, AAA64832.1, AAA83030.1, AAA67204.1, AAA18478.1, AAA52708.1, AAA40546.1, XP_002828698.1, XP_002827759.1, XP_002807841.1, AAA67349.1, XP_233737.5, XP_001077293.2, AAB36305.1, AAQ14910.1, AAQ14909.1, AAQ14908.1, AAQ14907.1, AAQ14906.1, AAQ14901.1, AAQ14898.1, AAQ14897.1, AAQ14896.1, AAF18980.1, AAH15969.1, EFB12989.1, AAI13141.1, AAH30132.2, AAH08626.1, ADA18203.1, ADA18202.1, AAP36234.1, AAP35500.1, AAO30128.1, AAH26338.1, AAS89259.1, AAH03097.1, AAF81280.1, AAB17532.1, AAA69862.1, AAA80011.1, AAB60661.1, AAA16920.1, AAA36035.1, EAW84091.1, EAW84086.1, 1H2Q_P, 1H2P_P, 1H03_Q, 1H03_P, 1IJ9_A, 1D3I_4, 1D3I_3, 1D3I_2, 1D3I_1, 1A5F_H, 1A5F_L, 1A6T_D, 1A6T_C, 1A6T_B, 1A6T_A, ACQ15346.1, ACQ15344.1, ACP57322.1, CAY39147.1, CAY39146.1, CAY39145.1, CAX14828.1, CAX14826.1, CAQ14148.1, CAQ14147.1, CAQ14145.1, CAG46633.1, CAG46611.1, BAG73299.1, CAJ18510.1, CAJ18454.1, 1Z7S_4, 1Z7S_3, 1Z7S_2, 1Z7S_1, BAG60348.1, BAG35520.1, ABM85957.1, ABM84711.1, DAA06142.1, DAA06141.1, CAP72055.1, BAF85799.1, BAD96939.1, BAD93115.1, ABU37676.1, ABU37675.1, ABU37674.1, EDL78332.1, EDL25153.1, EDL25151.1, CAM73181.1, ABM92232.1, ABM82769.1, AAQ14922.1, AAQ14905.1, AAQ14904.1, AAQ14902.1, ABL30031.1, ABL13876.1, CAA40441.1, CAL47730.1, CAE84094.1, CAE84091.1, CAA34622.1, AAX42182.1, AAX42181.1, AAX29641.1, AAX29640.1, AAX37087.1, AAX36636.1, AAX04661.1, AAQ80664.1, AAQ71936.1, AAQ70987.1, AAQ53651.1, AAQ53650.1, AAQ53649.1, AAQ53648.1, AAQ53647.1, AAQ53646.1, CAD97562.1, CAD97565.1, AAE22204.1, AAE22202.1, AAE20921.1, AAE20920.1, AAE20919.1, AAE10139.1, AAC89984.1, AAC89982.1, AAC87796.1, AAC87794.1, AAC19905.1, AAC19903.1, AAC19660.1, 225938, AAA55744.1, NP_570116.2, Q5NKV2.1, Q5NKV1.1, NP_570118.1, P41323.1, NP_001029170.1, 2V7D_S, 2V7D_R, 2V7D_Q, 2V7D_P, 2V7D_D, 2V7D_C, 2V7D_B, 2V7D_A, 2JF1_T, 2JF1_A, AAE18933.1, AAE18932.1, AAE18931.1, AAE18930.1, AAE18929.1, AAE18928.1, AAE18927.1, AAE18926.1, AAE18925.1, AAE18924.1, AAE18923.1, AAE18922.1, AAE18921.1, AAE18920.1, AAE18919.1, AAE18918.1, AAE18917.1, AAE18916.1, AAE18915.1, 3M6F_A, AAA60393.1, and AAA60392.1.

In one aspect, an ICAM-1 useful for compositions and methods described herein is glycosylated. In another aspect, an ICAM-1 useful for compositions and methods described herein is non-glycosylated. In one embodiment, a glycosylation can be naturally occurring. In another embodiment, a glycosylation can be artificially introduced to ICAM-1 through recombinant DNA technology generally known in the art.

In one aspect, an ICAM-1 useful for compositions and methods described herein is naturally modified. In one embodiment, a natural modification is a post-translational modification. In one embodiment, an ICAM-1 comprises a polypeptide containing the signal peptide portion of an ICAM-1. In another embodiment, an ICAM-1 comprises a polypeptide lacking the signal peptide portion of an ICAM-1.

In one aspect, an ICAM-1 useful for compositions and methods described herein has the amino acid sequence of SEQ. ID. NO.: 1 (Genbank Accession No. AAQ14901): MAPSSPRPALPALLVLLGALFPGPGNAQTSVSPSKVILPRGGSVLVTCSTSCDQPKLLGIETPLPKKELLLPGNNRKVYELSNVQEDSQPMCYSNCPDGQSTAKTFLTVYWTPERVELAPLPSWQPVGKNLTLRCQVEGGAPRANLTVVLLRGEKELKREPAVGEPAEVTTTVLVRRDHHGANFSCRTELDLRPQGLELFENTSAPYQLQTFVLPATPPQLVSPRVLEVDTQGTVVCSLDXLFPVSEAQVHLALGDQRLNPTVTYGNDSFSAKASVSVTAEDEGTQRLTCAVILGNQSQETLQTVTIYSFPAPNVILTKPEVSEGTEVTVKCEAHPRAKVTLNGVPAQPLGPRAQLLLKATPEDNGRSFSCSATLEVAGQLIHKNQTRELRVLYGPRLDERDCPGNWTWPENSQQTPMCQAWGNPLPELKCLKDGTFPLPIGESVTVTRDLEGTYLCRARSTQGEVTREVTVNVLSPRYEIVIITVVAAAVIMGTAGLSTYLYNRQRKIKKYRLQQAQKGTPMKPNTQATPP (SEQ. ID. NO.: 1). In another embodiment, an ICAM-1 is a peptide corresponding to the amino acid sequence AAQ14901, but lacking a signal peptide, which corresponds to the $1^{st}$ to $27^{th}$ amino acid residues of SEQ. ID. NO.: 1. In another embodiment, an ICAM-1 is a chimpanzee ICAM-1 protein. In another embodiment, an ICAM-1 has the amino acid sequence of SEQ. ID. NO.: 10 (Genbank Accession No. AAQ14896).

In one embodiment, an ICAM-1 useful for compositions and methods described herein is a fragment of an ICAM-1 protein. In one embodiment, a fragment of ICAM-1 protein has a biological activity equivalent to that of the ICAM-1 protein. In another embodiment, a fragment of ICAM-1 protein does not have a biological activity equivalent to that of the ICAM-1 protein. In another embodiment, a fragment of ICAM-1 protein is biological inactive.

In one aspect, an effect of an ICAM-1 on neprilysin expression is used to measure the biological activity of an ICAM-1. In one embodiment, an effect is a level of an increase in neprilysin expression. In another embodiment, an effect is a decrease in neprilysin expression. In one embodiment, a biological activity of an ICAM-1 fragment is measured as a percentage of the activity of another ICAM-1 serving as a standard for comparison. An ICAM-1 standard for comparison can be a full-length ICAM-1, truncated ICAM-1, mutated ICAM-1, post-translationally modified ICAM-1, or a fragment of an ICAM-1 different from the compared ICAM-1. Any ICAM-1 protein or polypeptide described herein can be used as a protein in comparison. A percentage of difference in biological activity can be about 5%, 10%, 15%, 20%, 25%, 30%, 35%, 40%, 45%, 50%, 55%, 60%, 65%, 70%, 75%, 80%, 85%, 90%, 95%, 100%, 105%, 110%, 115%, 120%, 125%, 130%, 135%, 140%, 145%, 150%, 155%, 160%, 165%, 170%, 175%, 180%, 185%, 190%, 195%, or 200%. In one embodiment, a biological activity of an ICAM-1 fragment is measured as a fold-increase or decrease of the activity of another ICAM-1 serving as a standard for comparison. A fold-increase or decrease can be about 2-fold, 2.5-fold, 3-fold, 4-fold, 5-fold, 7-fold, -fold, 10-fold, 20-fold, 30-fold, 50-fold, 100-fold, 200-fold, 500-fold, 800-fold, or 1000-fold.

In one embodiment, an ICAM-1 fragment comprises $28^{th}$ to $483^{rd}$ amino acids of SEQ. ID. NO.: 1. In another embodiment, an ICAM-1 fragment comprises $28^{th}$ to $380^{th}$ amino acids of SEQ. ID. NO.: 1. In another embodiment, an ICAM-1 fragment comprises $28^{th}$ to $300^{th}$ amino acids of SEQ. ID. NO.: 1. In another embodiment, an ICAM-1 fragment comprises $28^{th}$ to $200^{th}$ amino acids of SEQ. ID. NO.: 1.

Described herein is an ICAM-1 variant of SEQ. ID. NO.: 1 useful for a treatment of a neurological disorder. In one embodiment, a variant of SEQ. ID. NO.: 1 is a polypeptide having one or more amino acids substituted, deleted, or inserted. In another embodiment, the sequence identity of a variant to SEQ. ID. NO.: 1 is at least 80%, 82%, 85%, 87%, 89%, 90%, 93%, 95%, 96%, 97%, 98% or 99%. In another embodiment, the sequence identity of the extracellular domain of a variant to that of SEQ. ID. NO.: 1 is at least 80%, 82%, 85%, 87%, 89%, 90%, 93%, 95%, 96%, 97%, 98% or 99%. In another embodiment, the sequence identity of the intracellular domain of a variant to that of SEQ. ID. NO.: 1 is at least 80%, 82%, 85%, 87%, 89%, 90%, 93%, 95%, 96%, 97%, 98% or 99%. In another embodiment, the sequence identity of the transmembrane domain of a variant to that of SEQ. ID. NO.: 1 is at least 80%, 82%, 85%, 87%, 89%, 90%, 93%, 95%, 96%, 97%, 98% or 99%.

In one aspect, compositions and methods described herein comprise one or more isolated polypeptides of ICAM-1. In one embodiment, one or more isolated polypeptides of ICAM-1 are ICAM-1s of different amino acid sequences. In another embodiment, one or more isolated polypeptides of ICAM-1 are ICAM-1s of differently processed by post-translational modification process.

In another aspect, compositions and methods described herein comprise one or more ICAM-1 polypeptides attached to a cell. In one embodiment, one or more ICAM-1 polypeptides are covalently attached to a cell. In another embodiment, the polypeptides are embedded in cell membrane. A cell includes, but is not limited to, mammalian cell, bacterial cell, fungal cell, or an insect cell. In one embodiment, a cell is a human cell. In another embodiment, a cell is a human stem cell. In another embodiment, a cell is a human mesenchymal stem cell. In another embodiment, a cell is a human stromal cell. In another embodiment, a cell is an umbilical cord blood cell. An umbilical cord blood cell useful for compositions and methods described herein includes, but is not limited to, cells normally found in, or cultured from the cells normally found in the umbilical cord, umbilical cord blood, amniotic sac, and the placenta.

In another aspect, compositions and methods described herein comprise one or more ICAM-1 polypeptides and a cell secreting ICAM-1 polypeptides.

In another aspect, compositions and methods described herein comprise one or more ICAM-1 polypeptides conjugated with another biological material. A biological material includes, but is not limited to, various small peptides, another protein, a chemical means useful for isolating or identifying conjugated polypeptides (which are known as "tags" in the art).

In one aspect, ICAM-1 polypeptides described herein in are isolated from an organism, tissues or cells. In one embodiment, ICAM-1 is isolated from mesenchymal stem cells (MSCs) or a culture thereof. Examples of the source of mesenchymal stem cell include, but are not limited to, embryonic yolk sac, placenta, umbilical cord, umbilical cord blood, skin, peripheral blood, bone marrow, adipose tissue, muscle, liver, neural tissue, periosteum, fetal membrane, synovial membrane, synovial fluid, amniotic membrane, meniscus, anterior cruciate ligament, articular chondrocytes, decidous teeth, pericyte, trabecular bone, infra patellar fat pad, spleen and thymus. In one embodiment, a source of MSCs is an umbilical cord blood-derived MSC or a bone marrow-derived MSC.

Described herein is a method of isolating MSCs from umbilical cord blood. In one embodiment, ICAM-1 is isolated by harvesting umbilical cord blood-derived MSCs. In one embodiment, umbilical cord blood-derived MSCs are isolated by centrifugation. In another embodiment, umbilical cord blood-derived MSCs are isolated by fluorescence-activated cell sorting. In another embodiment, umbilical cord blood-derived MSCs are isolated by using various tags including magnetic beads. In another embodiment, umbilical cord blood-derived MSCs are isolated by using MSC-specific antibodies. In some aspects, other methods of cell separation and isolation can be used. These methods, which are well known in the art, include, but are not limited to, separating by size, weight, or shape of a cell, differences on the types of cell surface molecules, resistance or attraction to chemicals, proteins, or other cells, and other physical or chemical properties useful for distinguishing MSCs from non-MSCs.

In one aspect, ICAM-1 is produced by a recombinant DNA technology. In one embodiment, nucleic acids encoding ICAM-1or a fragment thereof are cloned into an appropriate recombinant expression system. In one embodiment, a recombinant expression system is bacterial expression system. In another embodiment, a recombinant expression system is an insect-cell expression system. In another embodiment, a recombinant expression system is a mammalian expression system. In one embodiment, a bacterial recombinant expression system is a pET vector expression system. In one embodiment, a pET vector useful for expressing ICAM-1 described herein is pET-28a plasmid DNA. In another embodiment, a bacterial recombinant expression system useful for compositions described herein is a pET vector containing nucleic acids encoding an ICAM-1 having the nucleotide sequence of SEQ. ID. NO.: 2 (GenBank Accession No. NM_000201), or a fragment thereof: caagcttagcctggccgg-gaaacgggaggcgtggaggccgggagcagcccccggggtcatcgccctgcc-accgccgcccgattgcttagcttgaaattccggagctgaagcggccagcgagg-gaggatgaccctctcggcccgggcaccctgtcagtccggaaataactgcagcatt-tgttccggagggggaaggcgcgaggtttccgggaaagcagcaccgcccccttggc-ccccaggtggtagcgctaaaggatcacgcgccccagtcgacgctgagctcctct-gctactcagagttgcaacctcagcctcgctatggctcccagcagccccccggcccg-cgctgcccgcactcctggtcctgctcggggctctgttcccaggacctggcaatgc-ccagacatctgtgtccccctcaaaagtcatcctgccccggggaggctccgtgctg-gtgacatgcagcacctcctgtgaccagcccaagttgttgggcatagagaccccgtt-gcctaaaaaggagttgctcctgcctgggaacaaccggaaggtgtatgaactgag-caatgtgcaagaagatagccaaccaatgtgctattcaaactgccctgatgggcagt-caacagctaaaaccttcctcaccgtgtactggactccagaacgggtggaactggc-accccctcccctcttggcagccagtgggcaagaaccttaccctacgctgccaggtg-gagggtggggcaccccgggccaacctcaccgtggtgctgctccgtggggagaa-ggagctgaaacgggagccagctgtgggggagcccgctgaggtcacgaccacg-gtgctggtgaggagagatcaccatggagccaatttctcgtgccgcactgaactgg-acctgcggccccaagggctggagctgtttgagaacacctcggcccccctaccagc-tccagaccttttgtcctgccagcgactcccccacaacttgtcagcccccgggtccta-gaggtggacacgcaggggaccgtggtctgttccctggacgggctgttcccagtct-cggaggcccaggtccacctggcactgggggaccagaggttgaaccccacagtc-acctatggcaacgactccttctcggccaaggcctcagtcagtgtgaccgcagagg-acgagggcacccagcggctgacgtgtgcagtaatactggggaaccagagccag-gagacactgcagacagtgaccatctacagctttccggcgcccaacgtgattctga-cgaagccagaggtctcagaagggaccgaggtgacagtgaagtgtgaggcccac-cctagagccaaggtgacgctgaatggggttccagcccagccactgggcccgag-ggcccagctcctgctgaaggccaccccagaggacaacgggcgcagcttctcctg-ctctgcaaccctggaggtggccggccagcttatacacaagaaccagacccgga-gcttcgtgtcctgtatggcccccgactggacgagagggattgtccgggaaactgg-acgtggccagaaaattcccagcagactccaatgtgccaggcttggggggaacccat-tgcccgagctcaagtgtctaaaggatggcactttcccactgcccatcggggaatca-gtgactgtcactcgagatcttgagggcacctacctctgtcgggccaggagcaatg-ggcactgcaggcctcagcacgtacctctataaccgccagcggaagatcaagaaa-tacagactacaacaggcccaaaaagggaccccatgaaaccgaacacacaagc-cacgcctccctgaacctatcccgggacagggcctcttcctcggccttcccatattg-gtggcagtggtgccacactgaacagagtggaagacatatgccatgcagctacacc-taccggccctgggacgccggaggacagggcattgtcctcagtcagatacaacag-catttggggccatggtacctgcacacctaaaacactaggccacgcatctgatctgta-gtcacatgactaagccaagaggaaggagcagactcaagacatgattgatggatgt-taaagtctagcctgatgagagggggaagtggtgggggagacatagccccaccatg-aggacatacaactgggaaatactgaaacttgctgcctatttgggtatgctgaggccc-cacagacttacagaagaagtggccctccatagacatgtgtagcatcaaaacacaa-aggcccacacttcctgacggatgccagcttgggcactgctgtctactgaccccaa-cccttgatgatatgtatttattcatttgttatttttaccagctatttattgagtgtcttttatgta-ggctaaatgaacataggctctggcctcacggagctcccagtcctaatcacattca-aggtcaccaggtacagttgtacaggttgtacactgcaggagagtgcctggcaaaa-agatcaaatggggctgggacttctcattggccaacctgcctttccccagaagggagt-gatttttctatcggcacaaaagcactatatggactggtaatggttacaggttcagaga-ttacccagtgaggccttattcctcccttccccccaaaactgacaccttgttagccac-ctccccacccacatacatttctgccagtgttcacaatgacactcagcggtcatgtctg-gacatgagtgcccagggaatatgcccaagctatgccttgtcctcttgtcctgtttgca-tttcactgggagcttgcactatgcagctccagtttcctgcagtgatcagggtcctgca-agcagtggggaagggggccaaggtattggaggactccctcccagctttggaagc-ctcatccgcgtgtgtgtgtgtgtgtatgtgtagacaagctctcgctctgtcacccagg-ctggagtgcagtggtgcaatcatggttcactgcagtcttgacctttgggctcaagtg-atcctcccacctcagcctcctgagtagctgggaccataggctcacaacaccacac-ctggcaaatttgatifittifittificcagagacggggtctcgcaacattgcccagact-tcctttgtgttagttaataaagctttctcaactgccaaa (SEQ. ID. NO.: 2). In one embodiment, a bacterial cell useful for expressing ICAM-1 is E. coli BL21 variants. In one embodiment, a variant is E. coli BL21 (DE3). In one embodiment, the bacterial expression of recombinant ICAM-1 is induced by treating the transformed bacterial cells with IPTG.

Described herein is a pharmaceutical composition useful for the prevention or treatment of a neurological disorder. In one embodiment, a neurological disorder is a disease caused by any one selected from the group consisting of formation of amyloid-beta plaque in neurons, hyperphosphorylation of tau protein in neurons, damage to neurites, reduction in expression of neprilysin in neurons, and a combination thereof. In another embodiment, a neurological disorder is selected from the group consisting of Alzheimer's disease, Parkinson's disease, depression, epilepsy, multiple sclerosis, mania, Lou Gehrig's disease, mild cognitive impairment, multi-infarct dementia, and dementia with Lewy bodies.

In one aspect, ICAM-1 polypeptides described herein are administered to a subject to intervene with the progress of a neurological disorder. In one embodiment, ICAM-1 polypeptides described herein are administered to a subject suffering from Alzheimer's disease to slow or, stop, or reverse the progress of Alzheimer's disease. In one embodiment, a dose of ICAM-1 polypeptides is administered to a subject once. In another embodiment, a dose of ICAM-1 poplypeptides is administered to a subject on a regular interval for an extended period of time. An interval can be a few days, weeks, months, or years. In another embodiment, an initial dose of ICAM-1 polypeptides is administered to a subject, and then the follow up dose is either reduced or increased depending on the clinical outcome of the subject. A clinical outcome is measured by neuropsychological tests including, but is not limited to, self-evaluation, clinical questionnaires, such as clinical dementia scoring, or a mental state examination.

Compositions described herein can be delivered via a topical administration or a systematic administration. In one embodiment, compositions described herein are administered in an amount effective for preventing or treating a neurological disorder. In one embodiment, an effective amount is determined by clinical trials. An effective dose can vary depending on various circumstances including, but is not limited to, types of neurological conditions, manufacturing processes, formulations, routes of administrations, and types of excipients.

A pre-dementia syndrome exhibiting mild cognitive impairment may be diagnosed using a neuropsychological test. It has been reported that about 12% of patients with mild cognitive impairment progress to Alzheimer's disease per year. Surprisingly, about 80% of patients with mild cognitive impairment progress to Alzheimer's disease after 6 years in the absence of any treatment. Thus, when the ICAM-1 protein, or the fragment or the variant thereof, according to the present invention is administered to patients with mild cognitive impairment, the progress to Alzheimer's disease may be prevented or delayed.

In one aspect, compositions described herein are administered in combination with other remedies or therapies effective on the prevention or treatment of Alzheimer's disease, Parkinson's disease, depression, epilepsy, multiple sclerosis, mania, Lou Gehrig's disease, mild cognitive impairment, multi-infarct dementia, or dementia with Lewy bodies. In one embodiment, compositions described herein are administered concomitantly with other remedial compositions or therapies. In another embodiment, compositions described herein are formulated to contain other remedial compositions known to be effective on Alzheimer's disease, Parkinson's disease, depression, epilepsy, multiple sclerosis, mania, Lou Gehrig's disease, mild cognitive impairment, multi-infarct dementia, or dementia with Lewy bodies.

Compositions described herein can contain pharmaceutically acceptable additives in addition to the effective ingredients. A formulation for parenteral administration such as an injection formulation or a topical administration formulation can be used. For example, a formulation for parenteral administration can be used in the form of an injection formulation of a sterile solution or suspension, if required, employing water or other pharmaceutically acceptable solvents. For example, a unit dosage formulation may be prepared using a pharmaceutically acceptable carrier or medium, e.g., sterile water, saline, vegetable oil, an emulsifier, a suspension, a surfactant, a stabilizer, an excipient, a vehicle, a preservative, and a binder. The parenteral administration can include a topical administration and a systematic administration. The topical administration can be performed by directly administering the pharmaceutical formulation into an injury region or peripheral regions of the injury region, for example, brain or spinal cord, peripheral regions thereof, or opposite regions thereof. The topical administration can include intra-nasal administration and intra-arterial administration. The systematic administration can be performed by administering the pharmaceutical formulation into spinal fluid, vein or artery. The spinal fluid includes cerebrospinal fluid. The artery may be a region for supplying blood to the injury region. In one embodiment, the administration is performed according to a method disclosed in e.g., Douglas Kondziolka, Pittsburgh, *Neurology*, Vol. 55, pp. 565-569, 2000, which is incorporate herein in its entirety. In one embodiment, the skull of a subject is incised to make a hole having a diameter of about 1 cm, and a suspension of ICAM-1 in a Hank's balanced salt solution (HBSS) is injected through the hole with a long-needle syringe and a stereotactic frame used to inject the suspension into the target region. A dose of the ICAM-1 may range from 500 to 1000 ng/kg (body weight) per day, which can be administered in a single dose or in divided doses.

Described herein is a method of increasing the expression of neprilysin in neurons, comprising co-culturing with neurons an ICAM-1 (intercellular adhesion molecule-1) protein, or a fragment or a variant thereof. In one embodiment, neprilsyin expression is increased by culturing ICAM-1 with neurons for less than a day, two days, three days, four days, five days, six days, seven days, nine days, or twelve days. In another embodiment, neprilsyin expression is increased by culturing with neurons for more than twelve days. In one embodiment, ICAM-1 is added to a media containing neurons and co-cultured. In another embodiment, ICAM-1 expressing cells are added to a media containing neurons and co-cultured. In another embodiment, ICAM-1 or ICAM-1 expressing cells and the neurons are co-cultured in a separate compartment of a culture device that allows the flow of nutrients, but not proteins, ligands, or other cellular products, either secreted by the cells in the culture or added to each compartment of a culture device.

Described herein is a method of increasing the expression of neprilysin in a subject, comprising administering to the subject an ICAM-1 (intercellular adhesion molecule-1) protein, or a fragment or a variant thereof In one embodiment, the administration is a topical administration. In another embodiment, the administration is a systematic administration. In one embodiment, an effective amount for increasing the expression of neprilysin is administered. In one embodiment, a formulation comprising an effective amount of ICAM-1 further comprises additives selected from the group consisting of water, culture medium, buffer, and an excipient.

EXAMPLES

Hereinafter, the present invention is described in more detail. The following Examples are given for the purpose of illustration only, and are not intended to limit the scope of the invention.

Example 1

In Vitro Efficacy of ICAM-1 Protein on NEP Expression

A recombinant ICAM-1 protein having the amino acid sequence of SEQ. ID. NO.: 1 was obtained from R&D SYS- TEMS (USA), and BV2 cells were obtained from Seoul National University (Korea). BV2 cells are immortalized cells prepared by infecting microglial cells of a mouse with v-raf/v-myc recombinant retrovirus, which express traits of activated microglial cells. BV2 cells were cultured in a serum-free DMEM medium and treated with the ICAM-1 recombinant protein at a concentration of 5, 10 and 50 ng/mL, respectively, followed by harvesting the cells after 24 hours. The harvested cells of each group were lysed using a sonicator (Branson Ultrasonics Corp.), and a protein extract was obtained therefrom by employing a buffer (9.8 M urea, 4% CHAPS, 130 mM dithiothreitol, 40 mM Tris-HCl, and 0.1% sodium dodecyl sulfate (SDS)). The extracted protein was quantified using the Bradford assay kit (Bio-Rad Laboratories, Hercules, Calif.), and 20 μg of the protein extract was resolved on SDS-PAGE and electrotransferred onto a nitrocellulose membrane. Each nitrocellulose membrane was incubated overnight with a primary antibody (anti-NEP antibody; R&D Systems, Minneapolis, Minn.), washed three times with PBS, and incubated with a secondary antibody (anti-goat IgG; Santa Cruz, USA). Then, the protein was visualized by an ECL kit (Amersham). Beta-actin was used as an internal control for quantification.

The results are shown on the left side of FIG. 1. The top left hand picture of the FIG. 1 is an immunoblot result and the bottom left hand graph of the FIG. 1 presents the strength of each band relative to the control (no treatment), measured by a densitometer (n=3, P<0.05).

As shown in the results, NEP expression was increased in ICAM-1 treatment groups compared to the control (no treatment group). Further, NEP expression level was proportional to the concentration of ICAM-1 proteins.

Meanwhile, in order to evaluate the efficacy of ICAM-1 proteins in terms of treating time, BV2 cells were treated with ICAM-1 protein (20 ng/mL) for 12, 24 and 36 hrs, respectively, and then NEP expression was analyzed as above.

The results are shown on the right side of FIG. 1. As shown in the results, NEP expression was increased in proportion to a treating time of ICAM-protein.

Example 2

In Vivo Efficacy of ICAM-1 Protein on NEP Expression

To evaluate the efficacy of ICAM-1 protein on NEP expression, 5 μL of PBS (n=4), or 500 or 1000 ng/kg of ICAM-1 protein in PBS (5 μL) (n=4/group) was administered into both hippocampi of each sacrificed anesthetized normal mice (B6C3F1/J, 13 weeks old, 30 g) by using a stereotaxic apparatus. After 7 days, the mice were sacrificed and brain tissue was collected. The brain tissue was lysed to obtain a protein extract and the extract was analyzed for NEP expression, as in Example 1.

Figure 2:
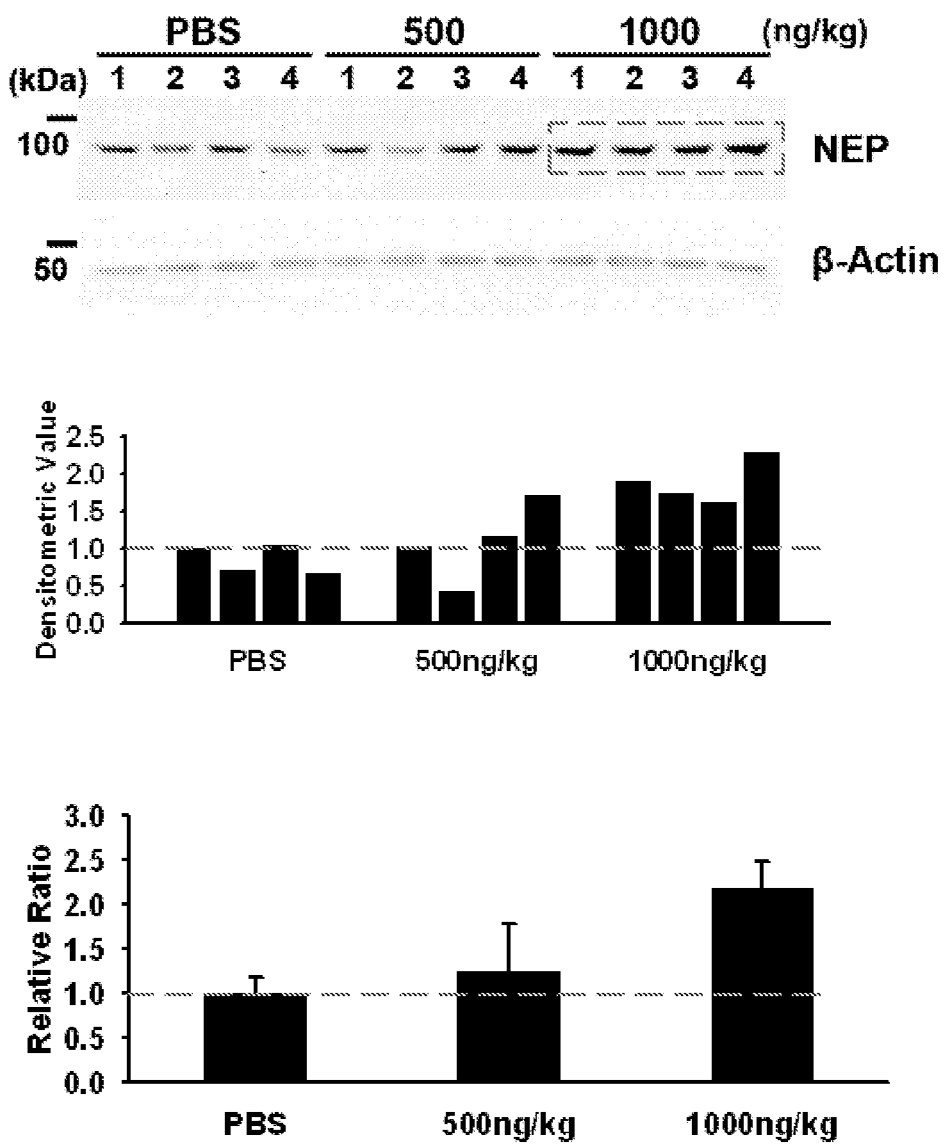
FIG. 2 illustrates the effect of ICAM-1 on the expression of neprilysin in hippocampus.

The results are shown in FIG. 2. As shown in FIG. 2, NEP expression was increased in ICAM-1 treatment groups compared to the control (no treatment group). In particular, the NEP expression level of the treated group with 1000 ng/kg of ICAM-1 was more than double that of control (PBS) (P=0.005).

Example 3

Effect of ICAM-1 on Amyloid-Beta42

In order to investigate the effect of ICAM-1 on the degradation of amyloid-beta42, the following experiments were carried out. Specifically, BV2 cells cultured in a serum-free DMEM medium were pretreated with ICAM-1 protein (5 or 10 ng/mL) and amyloid-beta42 (10 μM) at the same time and were further cultured for 24 hours. The level of amyloid-beta42 in the culture medium was measured using an ELISA kit (Wako Pure Chemical Industries Ltd. Japan). The results are shown in FIG. 3.

Figure 3:
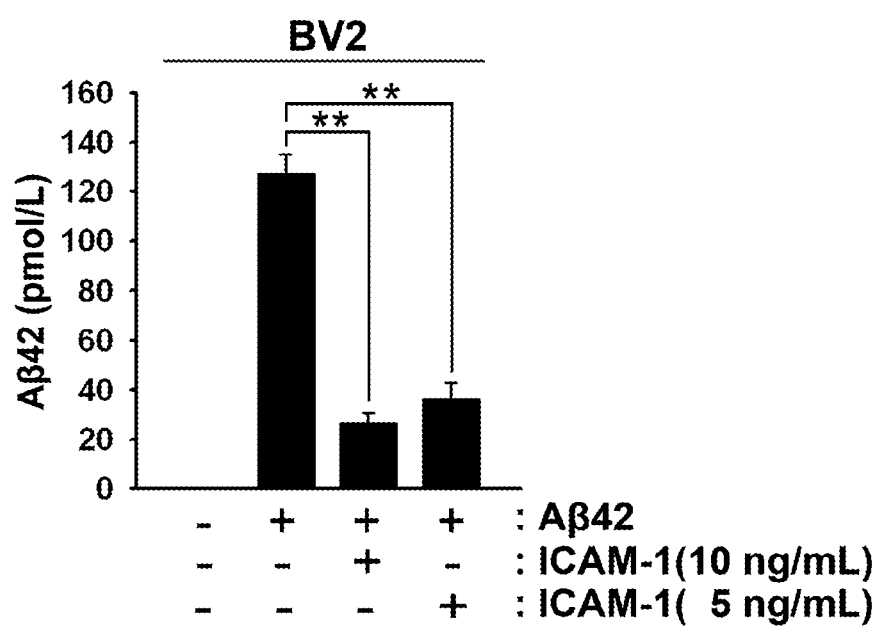
FIG. 3 illustrates the effect of ICAM-1 on amyloid-beta42.

As shown in FIG. 3, the levels of Aβ42 were significantly decreased in groups treated with ICAM-1 protein compared to the control. In particular, for ICAM-1-treated groups, the reduction of Aβ42 was proportional to the concentration of ICAM-1 protein. The results indicate that NEP induced by ICAM-1 protein degrades Aβ42.

Example 4

Preparation of ICAM-1 Fragments and Evaluation of Their Activities

Figure 4:
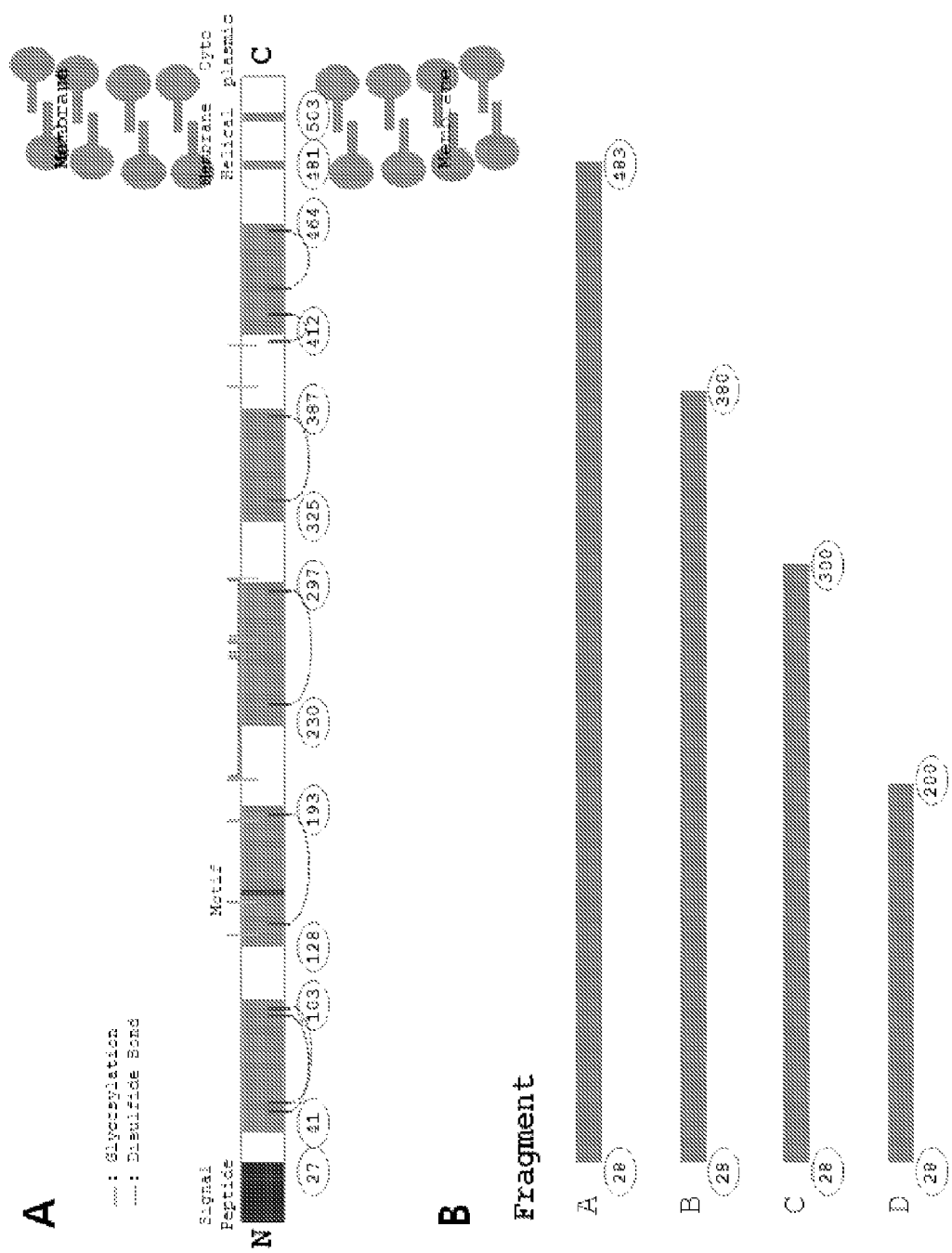
FIG. 4A illustrates the structure of an ICAM-1 protein.
FIG. 4B illustrates four ICAM-1 fragments prepared in Example 4.

In order to investigate an active domain responsible for ICAM-1 activity, four fragments were designed based on the location of ICAM-1 domains with a signal peptide removed (FIG. 4). In a pre-PCR for inducing a precise amplification of ICAM-1 gene, synthesized were primers for amplifying a full-length ICAM-1 gene, and primers for amplifying each gene fragment in which the recognition sites for restriction enzymes NdeI (NEB, USA) and BamHI (NEB, USA) were inserted.

The Pfu-PCR conditions were as follows: 40 cycles of 94° C. for 30 sec; 58~60° C. for 45 sec; 72° C. for 40 sec. The ICAM-1 fragments thus obtained and pET-28a plasmid DNA (Novagen®, USA) were digested with NdeI and BamHI. The primer sequences, annealing temperatures, and PCR product sizes are shown in Table 1.

TABLE 1

| Target gene | Primer sequence | Annealing temperature (° C.) | PCR product size (bp) |
|---|---|---|---|
| ICAM-1 | 5'-CCCCCAGGTGGCTAGCGCTA-3' (SEQ ID NO: 3) | 58 | 2153 |
| | 5'-GTGCCCAAGCTGGCATCCGT-3' (SEQ ID NO: 4) | | |
| A fragment | 5'-CCGCCG<u>CATATG</u>CAGACATCTGTGTCCCCC-3' (SEQ ID NO: 5) | 60 | 1404 |
| | 5'-CCCCCCCCCG<u>GGGATCC</u>TCATCAGATGACAATCTC-3' (SEQ ID NO: 6) | | |

TABLE 1-continued

| Target gene | Primer sequence | Annealing temperature (° C.) | PCR product size (bp) |
|---|---|---|---|
| B fragment | 5'-CCGCCG<u>CATATG</u>CAGACATCTGTGTCCCCC-3' (SEQ ID NO: 5) | 60 | 1089 |
| | 5'-CATTCG<u>GGATCC</u>TCATCACTGGCCGGCCACCTC-3' (SEQ ID NO: 7) | | |
| C fragment | 5'-CCGCCG<u>CATATG</u>CAGACATCTGTGTCCCCC-3' (SEQ ID NO: 5) | 60 | 846 |
| | 5'-CGG<u>GGATCC</u>TCATCACTCCTGGCTCTGGTTCCC-3' (SEQ ID NO: 8) | | |
| D fragment | 5'-CCGCCG<u>CATATG</u>CAGACATCTGTGTCCCCC-3' (SEQ ID NO: 5) | 60 | 549 |
| | 5'-CGGCGG<u>GGATCC</u>TCATCAAAACAGCTCCAGCCC-3' (SEQ ID NO: 9) | | |

Fragment A thus prepared encodes the $28^{th}$ to $483^{rd}$ amino acids in the amino acid sequence of ICAM-1 protein; fragment B, the $28^{th}$ to $380^{th}$ amino acids; fragment C, the $28^{th}$ to $300^{th}$ amino acids; and fragment D, the $28^{th}$ to $200^{th}$ amino acids.

Figure 5:
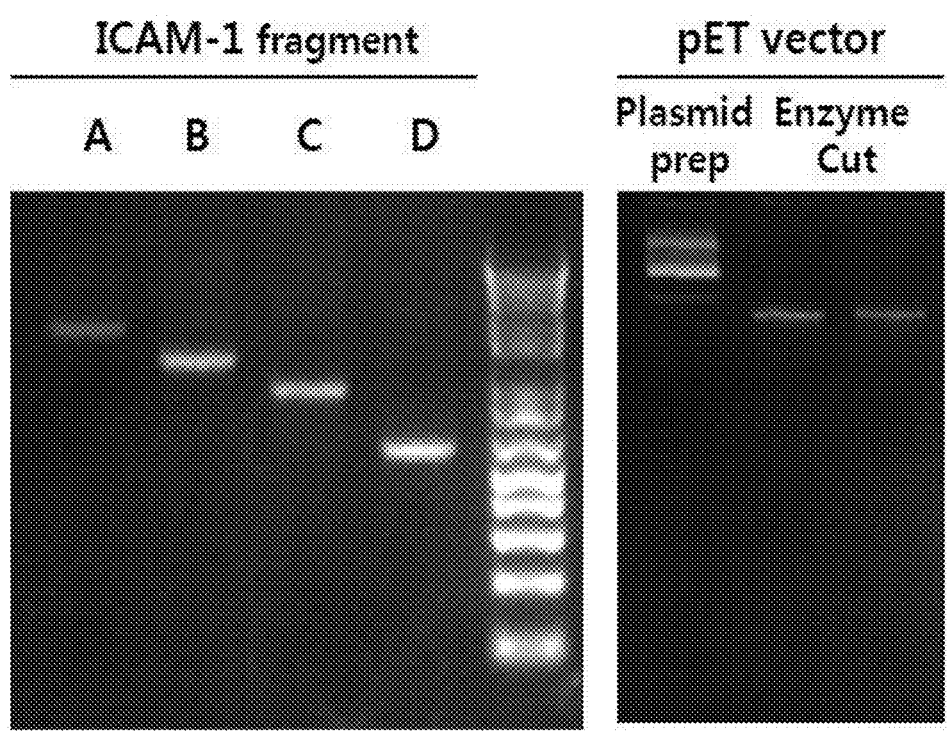
FIG. 5 illustrates four ICAM-1 genes encoding ICAM-1 fragments prepared in Example 4.

The sizes of the prepared ICAM-1 fragments were confirmed by an electrophoresis on 2% agarose gel (Invitrogen, USA). The electrophoresis results are shown in FIG. 5. As shown in FIG. 5, four fragments were confirmed to have the precise sizes.

Figure 6:
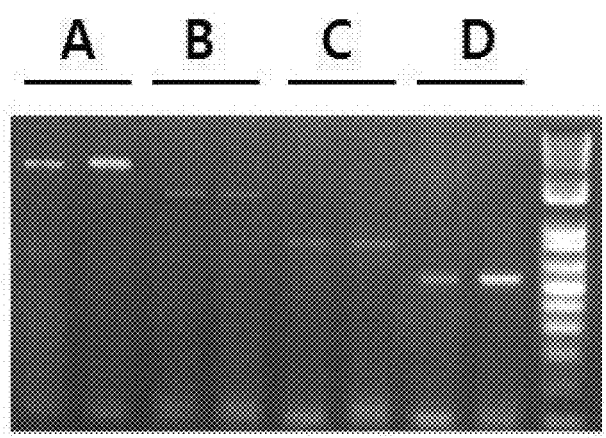
FIG. 6 illustrates nucleic acids obtained from an *E. coli* strain transformed with a plasmid containing ICAM-1 gene.

The fragments were purified using a Gel Extraction Kit (QIAGEN, USA) and mixed with pET-28a plasmid DNA (Novagen®, USA) treated with NdeI/BamHI, followed by ligation with T4 DNA Ligase (NEB, USA). *E. coli* BL21 (DE3) (Sigman, USA) was transformed with the ligated plasmid, and the transformant was cultured in LB agar medium (BD, USA). The proliferated single colonies were picked, placed into each PCR tube, and then subjected to PCR reaction. The amplified inserts were confirmed by an electrophoresis as above (FIG. 6), to select colonies. The chosen colonies were cultured in LB broth (BD, USA), and purified using QIAGEN® Plasmid Purification Kit (QIAGEN, USA) to obtain DNAs. The purified DNAs were digested with NdeI and BamHI, and then single colonies containing desired genes were confirmed again on 2% agarose gel with EtBr. The DNAs were purified using PCR Purification Kit (QIAGEN, USA) and the precise sequences of the inserted fragments were confirmed. The colonies of which DNA sequence was confirmed were cultured in LB broth in the presence of IPTG (Promega, USA). The resulting culture was centrifuged and the precipitated cells were treated with 8 M urea (pH 8.0) to lyse the cells. The recombinant protein was separated using Ni-NTA (nickel-nitrilotriacetic acid) agarose (QIAGEN, USA) based on the binding between 6× His attached to the N-terminal of the recombinant protein and Ni-NTA, and confirmed by SDS-PAGE and western blot.

Preparation Example 1

Formulation for Injection

To prepare a formulation for injection, 100 mg of ICAM-1 protein is dissolved in water and then mixed with 10 mL of 0.9% sterile saline. The mixture is incorporated into a dosage unit form suitable for injection.

Preparation Example 2

Formulation for Inhalation

To prepare a formulation for inhalation delivery, 20 mg of ICAM-1 protein is mixed with 50 mg of anhydrous citric acid and 100 mL of 0.9% sodium chloride solution. The mixture is incorporated into an inhalation delivery unit, such as a nebulizer, which is suitable for inhalation administration.

Preparation Example 3

Formulation for Nasal Delivery

To prepare a nasal spray solution, 10 g of ICAM-1 protein is mixed with 30 mL of a 0.05M phosphate buffer solution (pH 4.4). The solution is placed in a nasal administrator designed to deliver 100 μl of spray for each application.

What is claimed is:

1. A method of treating a neurological disease in a subject, wherein the disease is characterized by the abnormal accumulation of amyloid-beta plaques in neurons of the subject, comprising administering to the subject in need thereof an ICAM-1 (intercellular adhesion molecule-1) protein (SEQ ID NO: 1).

2. The method of claim 1, wherein the ICAM-1 protein induces expression of neprilysin (NEP).

3. The method of claim 1, wherein the ICAM-1 protein promotes degradation of amyloid-beta (Aβ).

4. The method of claim 1, wherein the neurological disease is selected from the group consisting of Alzheimer's disease, Parkinson's disease, epilepsy, and mild cognitive impairment.

* * * * *